United States Patent [19]

Averette

[11] Patent Number: 4,815,325

[45] Date of Patent: Mar. 28, 1989

[54] CAPILLARY FLUID INJECTORS

[75] Inventor: Julius P. Averette, Baker, La.

[73] Assignee: Dynatech Precision Sampling Corporation, Baton Rouge, La.

[21] Appl. No.: 184,763

[22] Filed: Apr. 22, 1988

[51] Int. Cl.$^4$ ............................................. G01N 35/06
[52] U.S. Cl. ............................... 73/864.21; 73/864.22; 73/864.24; 73/864.85
[58] Field of Search ........... 73/864.21, 864.81, 864.82, 73/864.83, 864.84, 864.85, 864.86, 864.87, 863.32, 864.22, 864.24, 864.25, 863.81, 864.23

[56] References Cited

U.S. PATENT DOCUMENTS

| | | | |
|---|---|---|---|
| 3,885,438 | 5/1975 | Harris, Sr. et al. | 73/863.81 |
| 3,940,995 | 3/1976 | Harris, Sr. et al. | 73/863.81 |
| 3,981,200 | 9/1976 | George et al. | 73/864.87 X |
| 4,044,616 | 8/1977 | Harris, Sr. et al. | 73/863.81 |
| 4,095,455 | 6/1978 | Karas et al. | 73/23.1 |
| 4,121,465 | 10/1978 | Harris, Sr. et al. | 73/863.81 |
| 4,351,802 | 9/1982 | Baylis et al. | 73/864.84 X |
| 4,621,534 | 11/1986 | Manari et al. | 73/864.86 |
| 4,713,974 | 12/1987 | Stone | 73/864.23 |
| 4,736,639 | 4/1988 | Averette | 73/864.24 |

Primary Examiner—Tom Noland
Attorney, Agent, or Firm—Llewellyn A. Proctor

[57] ABSTRACT

A capillary fluid injector, particularly an automated capillary fluid injector, for dispensing very small accurately measured quantities of a fluid into a medium. A capillary opening of adjustable volume is located on the dispensing end of the fluid injector assembly. The capillary opening of (A) an automated fluid injector, or fluid injector assembly can be loaded with a fluid specimen for subsequent injection via the combination of (B) an injector feed assembly comprised of a probe sub-assembly inclusive of a pair of hollow needles which provide a conduit for the pick up of said fluid specimen from a vial and transport of the fluid specimen to the fluid injector, and (C) a magazine for transporting one or more fluid specimen-containing septum sealed vials for pick up by the pair of hollow needles of the probe sub-assembly for delivery to the fluid injector via thrust of the probe through the septum of a vial, pressuring the contents of the vial by delivery of gas from a source through a first of the hollow needles of the probe sub-assembly to produce flow of fluid specimen from the vial into the second of the set of hollow needles for transport through the probe sub-assembly to the fluid injector.

16 Claims, 8 Drawing Sheets

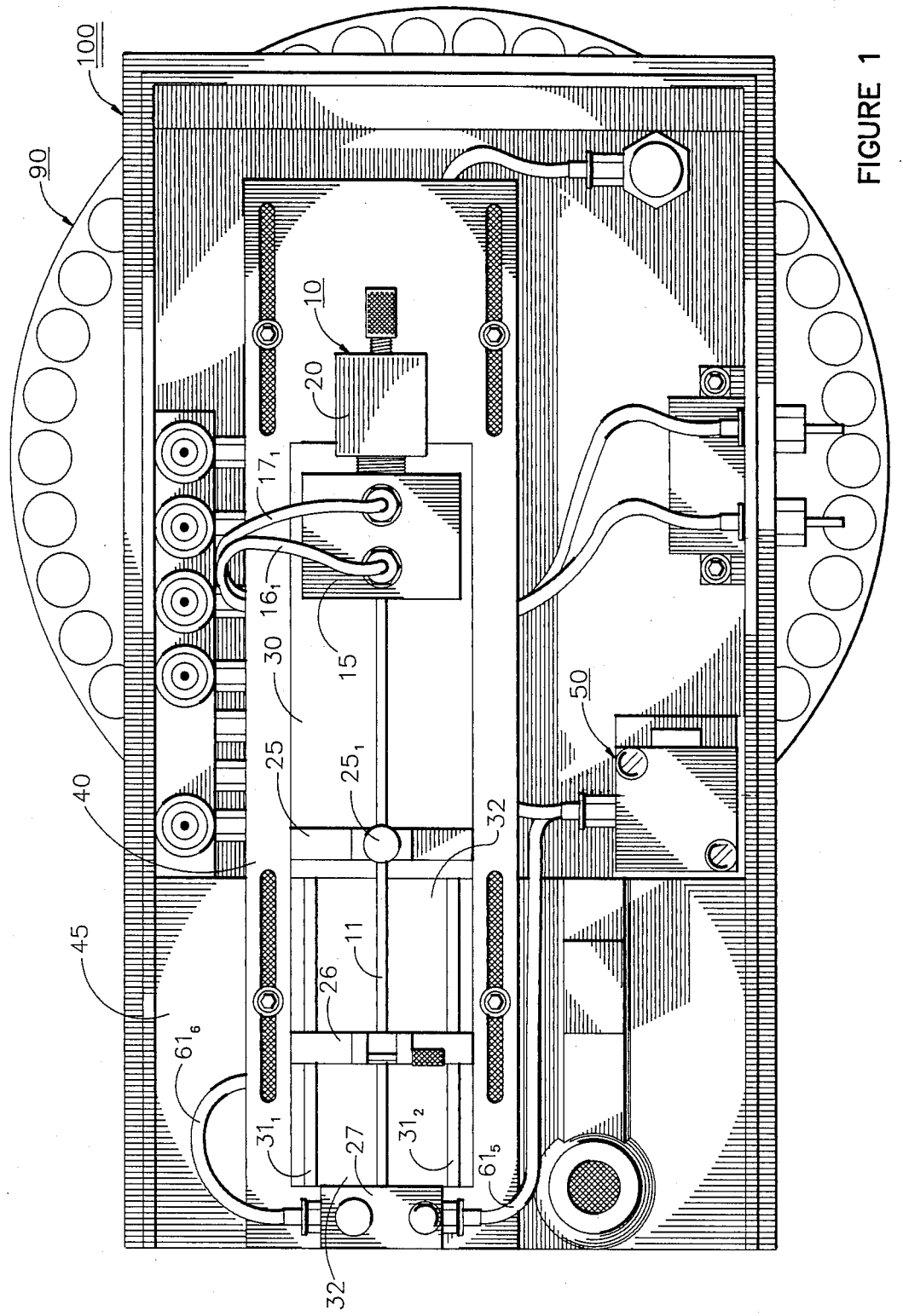

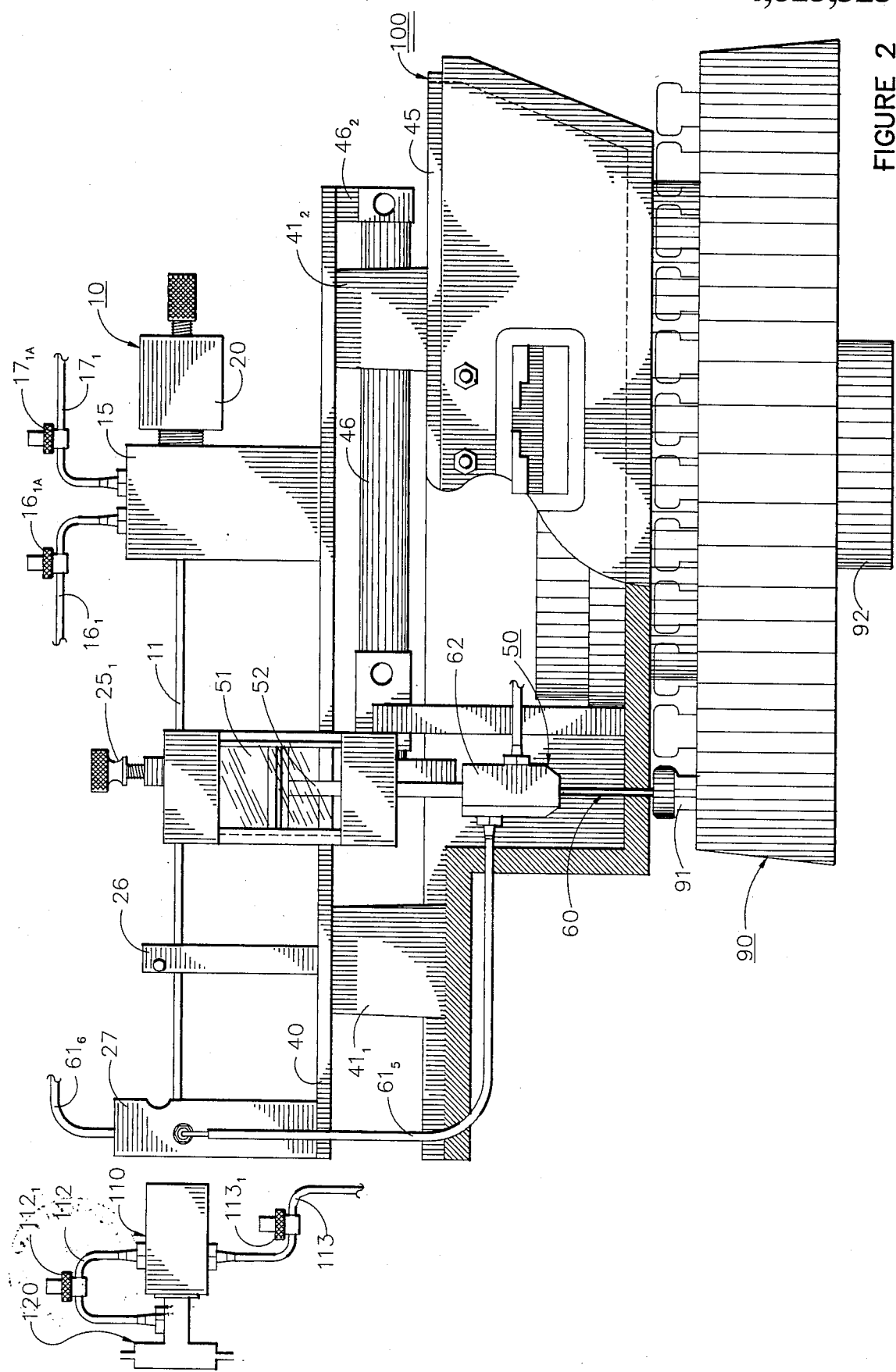

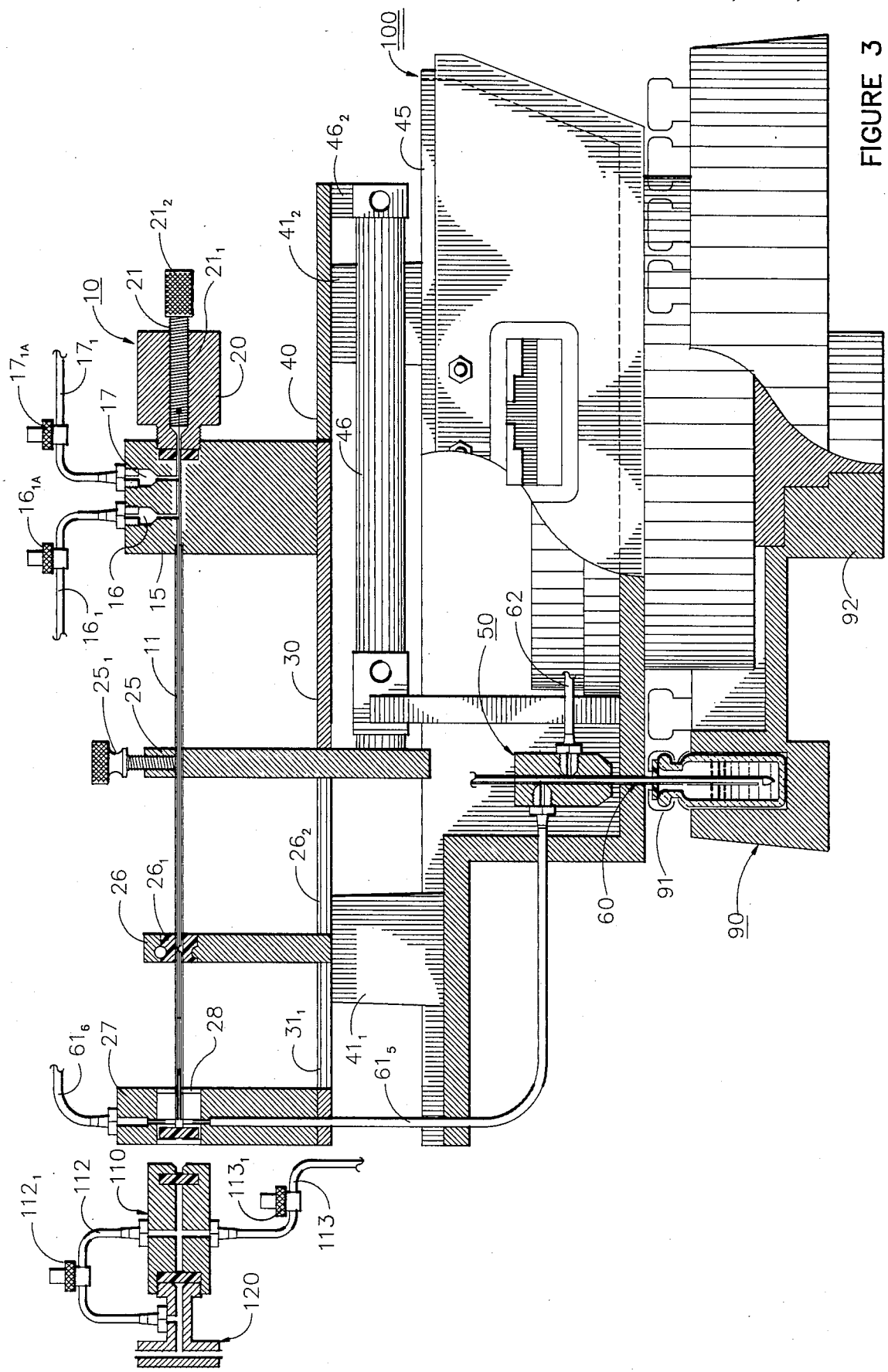

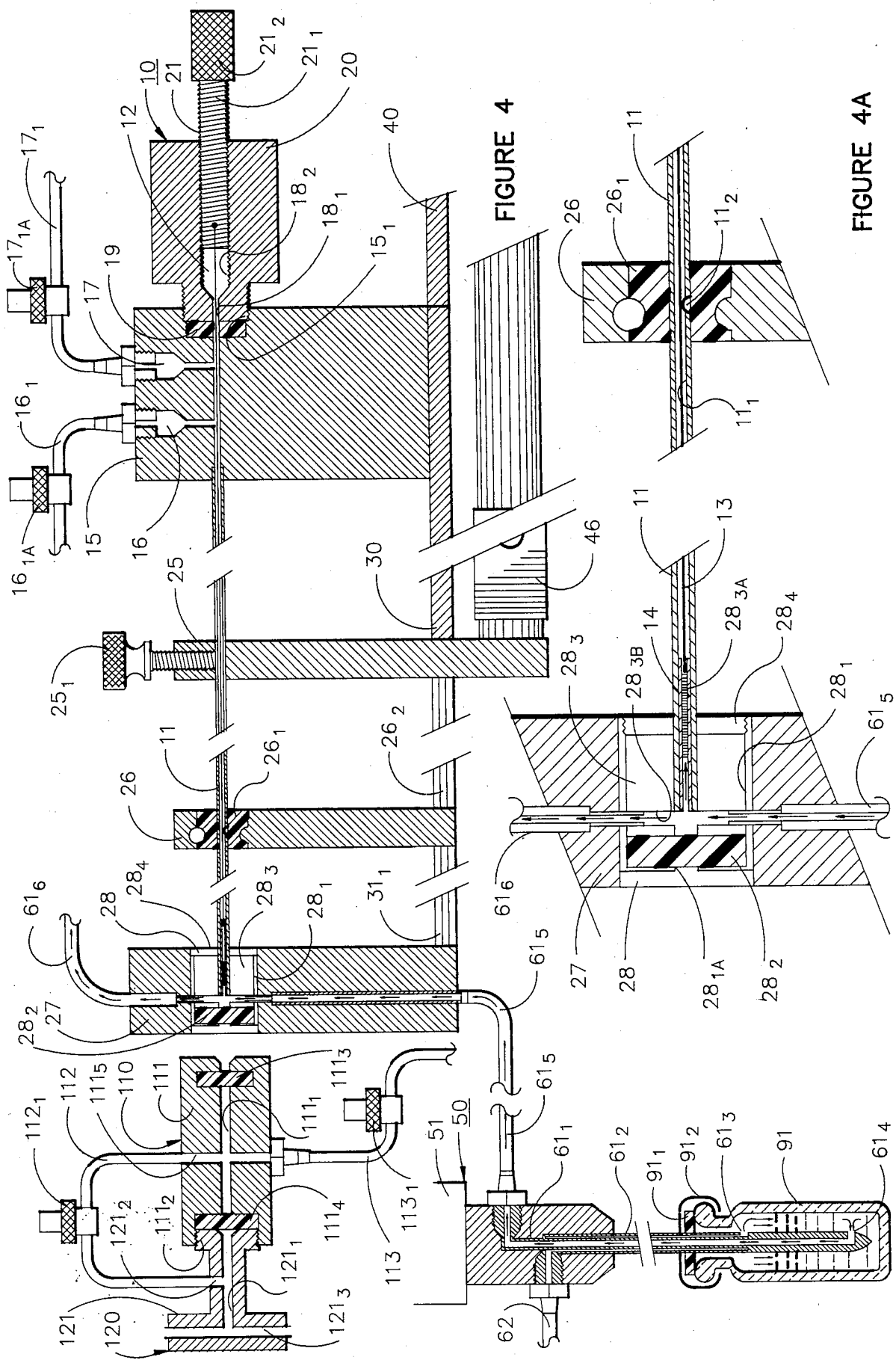

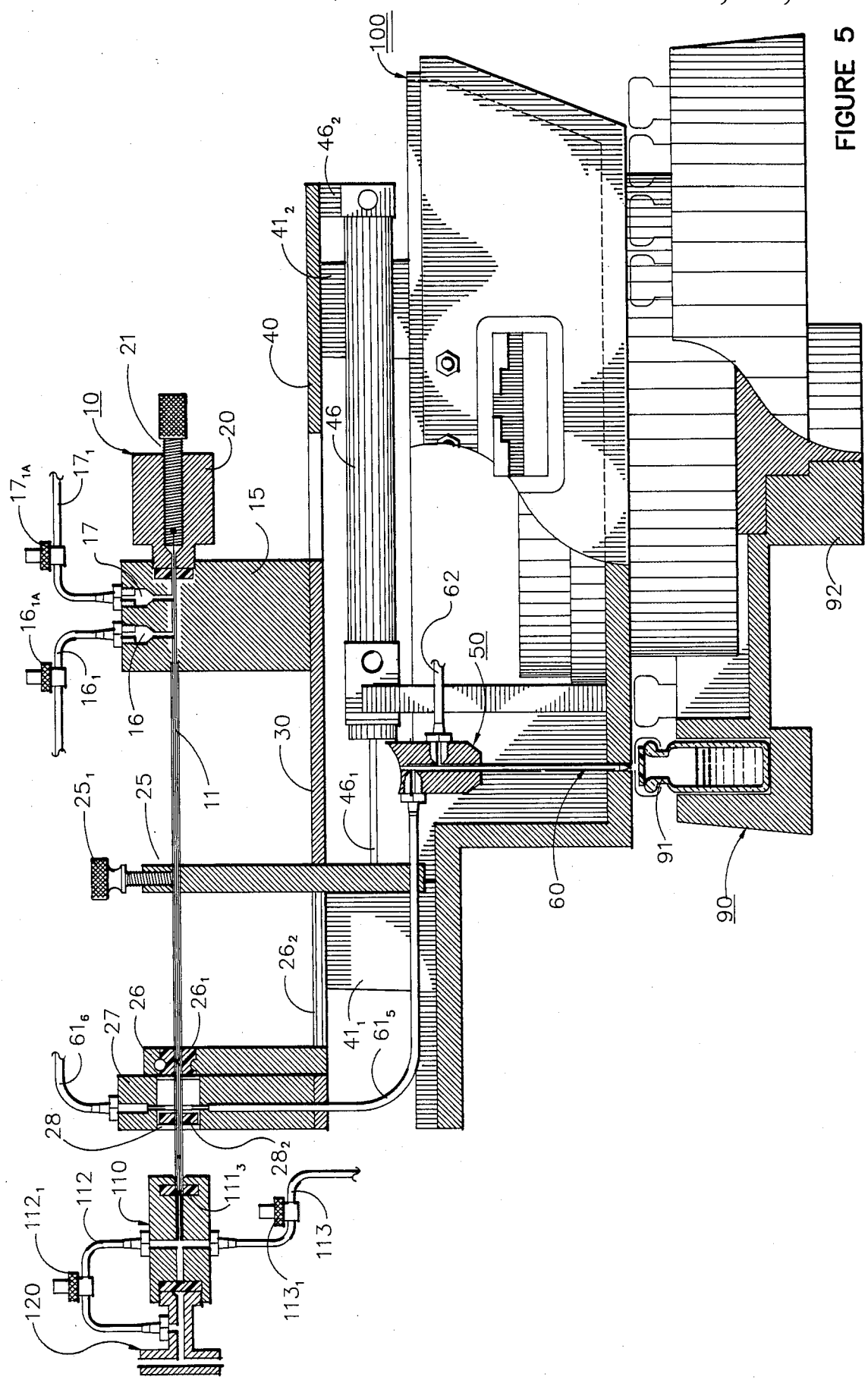

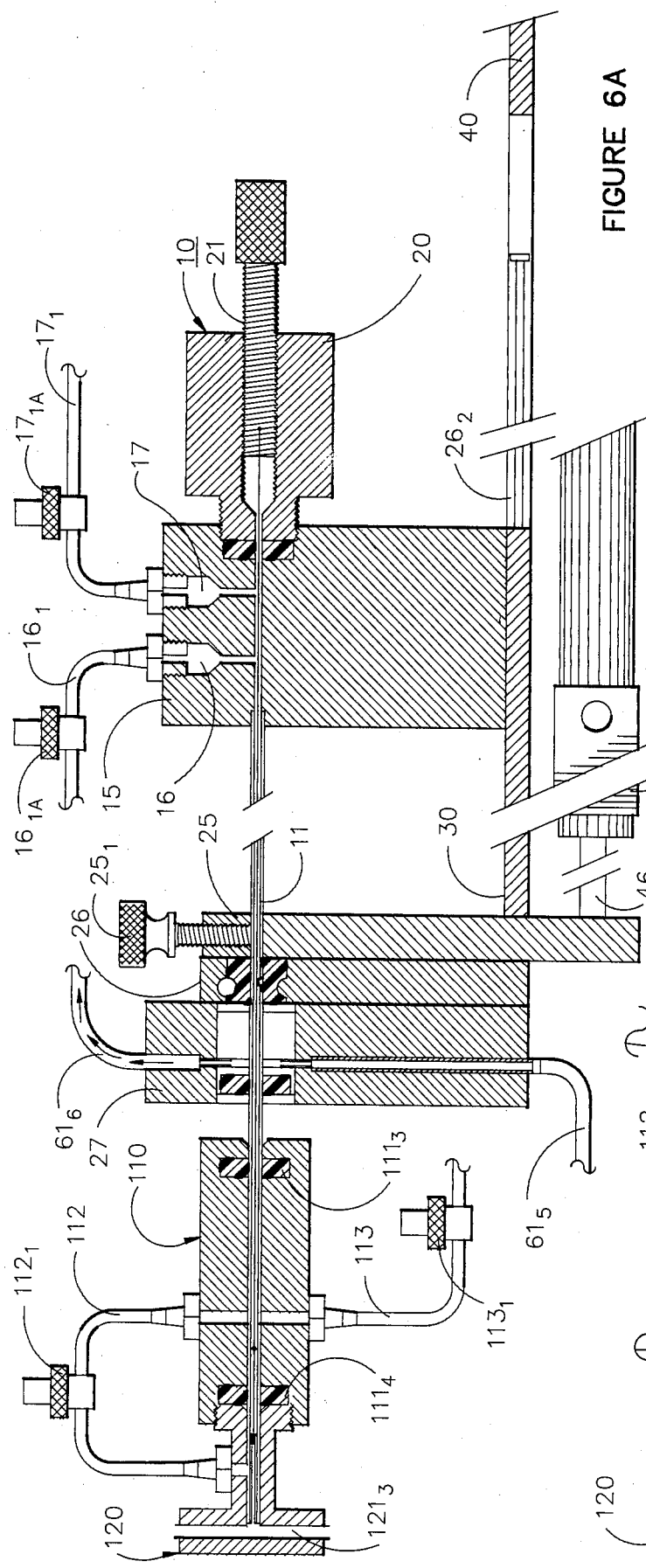
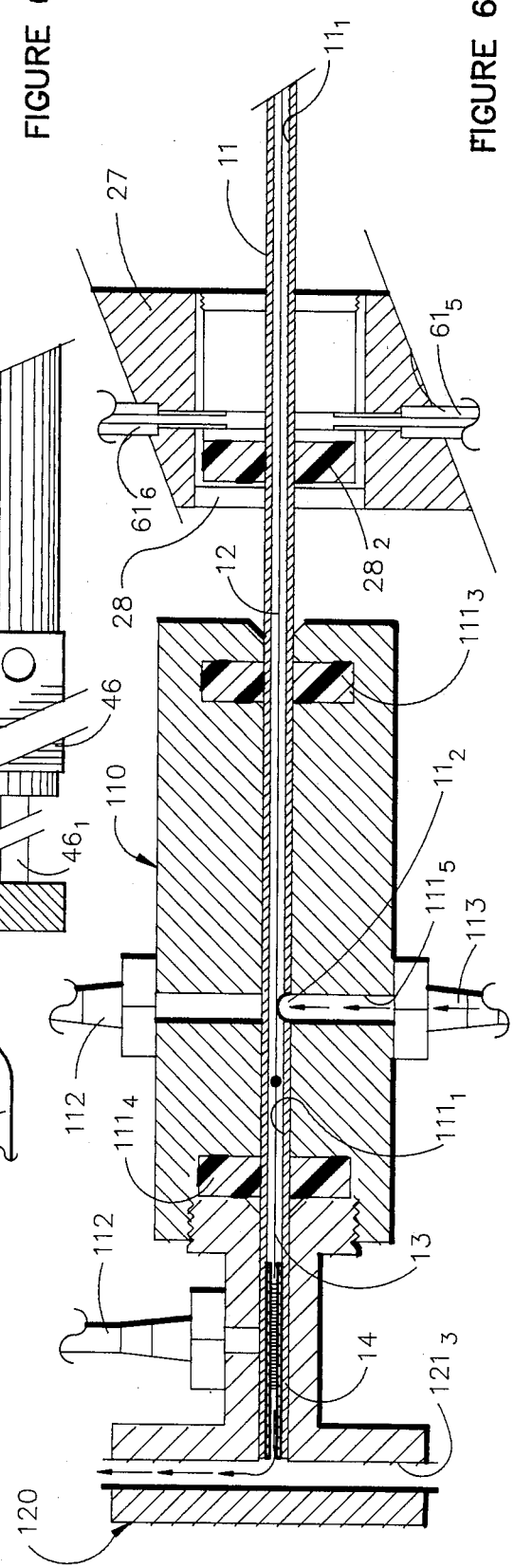
FIGURE 6A
FIGURE 6B

CAPILLARY FLUID INJECTORS

FIELD OF THE INVENTION

This invention relates to improvements in automatic fluid injectors, notably capillary fluid injection devices. Such apparatus is useful for automatically injecting very small, accurately measured quantities of a fluid into various media, e.g, the inlets of modern analytical instruments such as gas chromatographs or mass spectrographs.

BACKGROUND AND PROBLEMS

Automated fluid injection devices have gained wide acceptance by the industrial, scientific and medical communities due in large part to the advantages offered by modern data gathering techniques, and consequent reduction in operating manpower without loss in accuracy. Many such devices are capable of dispensing very small, accurately measured quantities of fluid specimens on the order of a few microliters, or very small fractions of a microliter, e.g., from about 0.01 to about 5 microliters, or fractional parts thereof into of a medium. One such type of fluid injector device can be characterized as an automated syringe, e.g., as described in U.S. Pat. No. 4,044,616. In the operation of the automated syringe, septum covered vials charged with portions of a fluid specimen are transported via a magazine to a station adjacent a probe assembly, the probe assembly picks up a specimen from a vial and a portion of the fluid specimen is conveyed via action of the probe assembly to the barrel of the syringe. Within the barrel of the syringe, a quantity of the fluid specimen is measured out and injected into the inlet of the analytical instrument.

Albeit very small quantities of fluid specimens can be measured out within the barrel of the syringe, and accurately injected, there is considerable impetus to further increase the capability of fluid injection devices to measure out and inject smaller, and yet smaller amounts of a fluid specimen with accuracy and precision.

Another class of fluid injection devices which has been used for measuring out and injecting small amounts of a fluid specimen with accuracy and precision into a medium are capillary dippers, or capillary injection devices. These devices differ as a class from syringes principally in that the fluid specimen is loaded via capillary action to a capillary opening of calibrated volume located on the terminal end of a probe. The measured quantity of the fluid specimen is injected not generally by positive displacement means but by insertion of the dispensing end of the probe into an inlet to an analytical instrument, and the fluid is flashed out of the calibrated opening, and conveyed by carrier gas to the instrument. The development of capillary injection devices, albeit these devices are particularly useful for measuring out and injecting very, very small quantities of a fluid specimen with accuracy and precision, has been far slower than that of automated syringes. There is indeed a particular need for the development of new and improved capillary fluid injectors, particularly automated capillary fluid injectors.

OBJECTS

It is, accordingly, a basic objective of this invention to satisfy this need.

In particular it is an object of this invention to provide a novel capillary fluid injector, particularly a novel automated capillary fluid injector.

A specific object is to provide a novel capillary fluid injector, particularly an automated capillary fluid injector, having an adjustable capillary bore, or bore the volume of which can be automatically adjusted by the operator to uptake preselected measured quantities of a liquid specimen for subsequent injection.

Another object is to provide a capillary fluid injector, preferably an automated capillary fluid injector, as characterized, provided with positive means for expelling, or injecting, the liquid specimen from the capillary bore, or capillary opening of the capillary fluid injector.

A more specific object is to provide capillary fluid injection apparatus generally as characterized which is capable of continuously cyclically serially withdrawing liquid specimens from prefilled septum covered vials, and positively injecting the specimens in seriatim in accurately measured, infinitesmally small reproducible quantities, into a medium.

A further object is to provide capillary fluid injection apparatus of simple and relatively inexpensive construction, particularly apparatus which can be readily serviced and operated, and is susceptible to rapid and mass production techniques.

SUMMARY OF THE INVENTION

These and other objects are achieved in accordance with the present invention which embodies improvements in capillary fluid injection devices, notably automatic capillary fluid injection devices which include (A) a capillary injector per se characterized generally as including an elongate tubular body, or hollow needle, at the forward or dispensing end of which is located a capillary chamber, or bore, a small diameter wire extending through the axial opening of said tubular body into said capillary chamber, or bore, and sample quantity adjustment means operatively associated with said small diameter wire for the extension and retraction of said wire into and out of said capillary chamber, or bore, to provide an annulus of capillary dimension within the capillary bore the volume of which can be varied to accommodate the quantity of the fluid specimen desired for injection into a medium. The small diameter wire is thus extended into a capillary bore the inside diameter of which is larger than the outside diameter of the wire to provide an annular opening between said inside surface of the bore and outside surface of the wire, and the wire can be extended or retracted via said sample quantity adjustment means over substantially the length of the capillary bore to adjust the volume of a fluid specimen loaded via capillary action into the capillary bore. In a further embodiment, an accurately measured amount of a fluid specimen loaded into the capillary chamber, or bore, can be positively expelled via a pressurized gas blown into the elongate tubular body, or hollow needle, to displace the fluid from the capillary chamber, or bore.

In a preferred embodiment the capillary fluid injection device (A), supra, is automated and the capillary chamber, or bore, of the capillary fluid injection device is automatically loaded with an accurately measured preselected quantity of a fluid specimen, and the fluid specimen then injected into a medium, respectively, by additional mechanisms which include (B) an injector feed assembly comprised of a probe sub-assembly which includes a pair of concentrically mounted hollow needles for the pick-up of said fluid specimen for filling the capillary chamber of said capillary fluid injector, and (C) a magazine for transporting one or more fluid specimen-containing septum sealed vials to a station adjacent the probe subassembly for pick-up by the pair of hollow needles for delivery to the capillary bore of said capillary fluid injector for subsequent injection into said medium.

REFERENCE TO THE FIGURES

The characteristics of a preferred automatic capillary fluid injector, and its principle of operation, will be more fully understood by reference to the following detailed description and to the attached drawing to which reference is made. Similar numbers are used in the different figures of the drawing to represent similar parts or components in the different figures, and subscripts are generally used with numbers where there are duplicate components. Where subscripts are dropped in the text, particularly after their introduction, the reference is intended in a generic sense.

In the drawing:

FIG. 1 depicts in plan a preferred automatic capillary fluid injector assembly which includes a housing containing (A) a capillary fluid injector, (B) an injector feed unit, inclusive of its probe assembly shown in lowered position, and (C) a motor driven carrousel type magazine, or feed tray.

FIG. 2 is a side elevation view of FIG. 1, with part of the housing cut away for clarity, this view again depicting (A) the capillary fluid injector, and the manner in which it is mounted, (B) the injector feed unit, with its probe assembly, and (C) the magazine, or feed tray.

FIG. 3 depicts a side elevation view of the automatic capillary fluid injector, partially in section, and the probe assembly of the injector feed unit, as in the preceding figures, is shown in lowered position as positioned in withdrawing a fluid specimen from a vial delivered by the magazine, or feed tray, for loading a fluid specimen into the capillary fluid injector.

FIGS. 4 and 4A depict in enlarged section essential features of the automatic capillary fluid injector, these specific views showing the initial loading of the capillary fluid injector with a portion of fluid-specimen delivered via the probe assembly of the injector feed unit.

FIGS. 5, 5A and 5B depict in section, in whole or in part, a side elevation view of the automatic capillary fluid injector, generally as shown in the preceding figures, except that the dispensing end of the capillary fluid injector, with fluid specimen loaded therein, has been advanced into an inlet chamber located in front of a septum inlet which leads into the analytical instrument.

FIGS. 6, 6A and 6B depict in section a side elevation view essentially as shown in FIGS. 5, 5A and 5B except that the dispensing end of the capillary fluid injector is further advanced into the inlet of the analytical instrument, and the fluid specmen is being injected.

DETAILED DESCRIPTION OF THE INVENTION

Figures 5A, 5B:
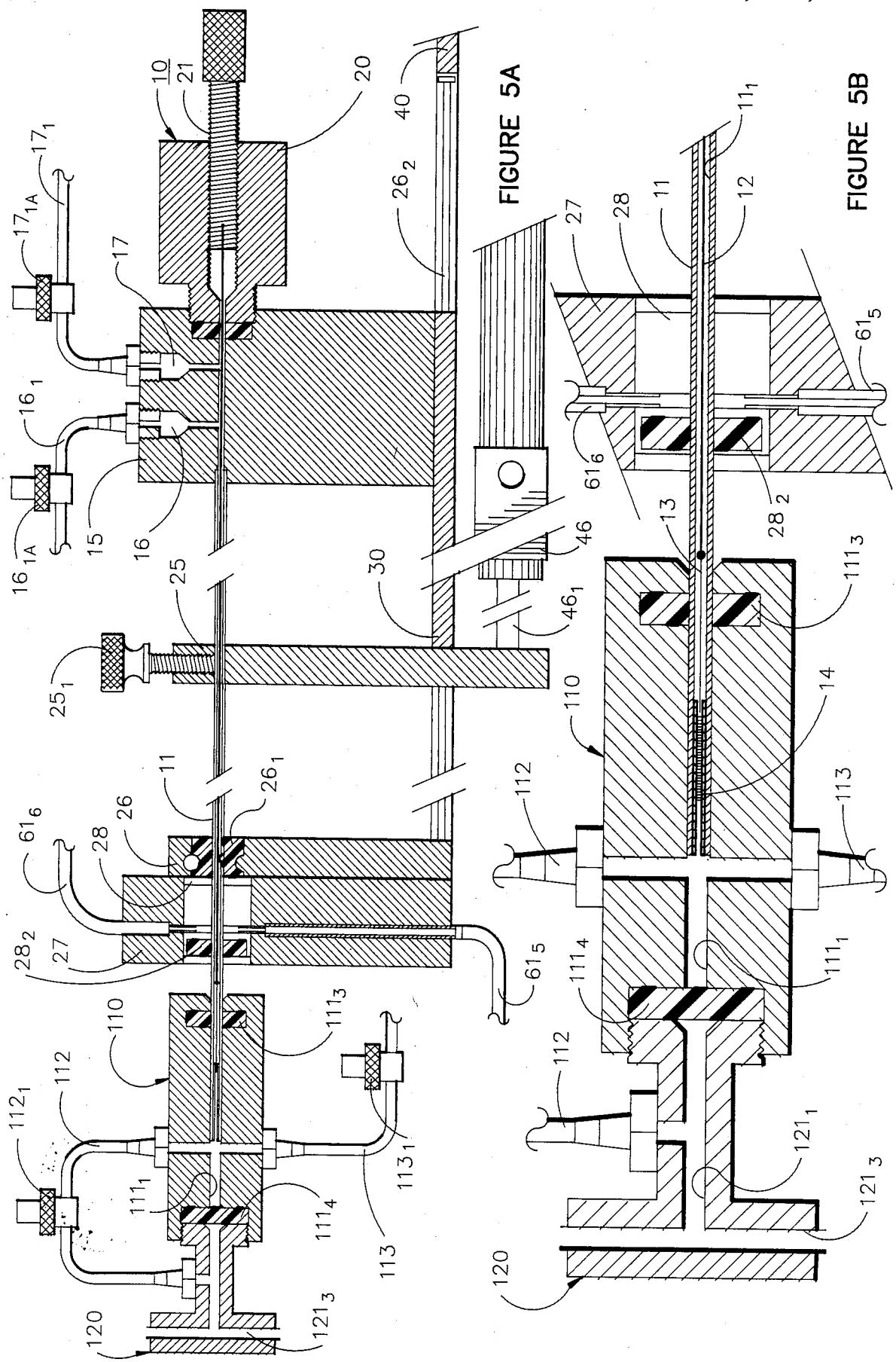

Reference is made to the figures, first generally to FIGS. 1-3 which show a preferred automatic capillary fluid injector 100. The principle sub-assemblies of the automatic capillary fluid injector 100 include (A) a capillary fluid injector assembly 10 which includes an elongate tubular body 11 at the rearward end of which is located sample quantity adjustment means 20 and at the forward, or dispensing end of which is located a capillary opening for containing an accurately measured fluid specimen for injection into the septum inlet 120, in-line therewith, via forward movement of the carriage 30 located within platform 40, (B) an injector feed assembly 50, inclusive of a reciprocable probe assembly 60 (or pair of concentric hollow probes) which is used to pick up a fluid specimen for delivery to the capillary fluid injector assembly 10, and (C) a magazine or carrousel type feed tray 90 for transporting one or a plurality of vials of fluid specimens to a location, or station, for pick up by said probe assembly 60. Portions of fluid specimens are picked up from the individual vials and injected in seriatim in accurately measured quantities via association with an inlet chamber 110 into e.g., an inlet 120 of an analytical instrument, via action of the capillary fluid injector assembly 10. The sub-assemblies (A), (B), and (C) are generally contained in whole or in part within a casing, housing or other enclosing structure and are responsive to known automatic control means not described. The principle features and overall function of these sub-assemblies and their relation one to another are generally as follows:

(A) The capillary fluid injector assembly 10, best shown by reference to FIGS. 3 through 6B includes generally a tubular section 11 within and through the axial opening $11_1$ of which there is extended a movable rod, suitably a manually adjustable or motorized rod or shaft 12, to the forward end of which is affixed a very small diameter wire 13. At the forward or dispensing end of the tubular section 11, over a short segment thereof (FIG. 4A; 5B), there is provided a capillary tube 14 or tube of very small internal diameter into which the small diameter wire 13 can be projected and retracted by the projection or retraction of the rod or shaft 12 to vary the volume of the capillary bore of tube 14 for containment of a fluid specimen. The rearward end of the tubular section 11 is affixed, and secured within a lateral opening through a metal block 15 providing an annulus $11_1$ with inlets 16, 17 into which a solvent, and gas (e.g., air), respectively, can be introduced via valved lines $16_1$, $17_1$, respectively, for cleaning and drying purposes. A sample quantity adjustment mechanism 20, described herein as manually adjustable, is mounted on the rearward face of the block 15, this mechanism being designed for precise movement and reciprocation of the wire 13 within the capillary opening of the tube 14 to adjust the capillary opening to the volume desired for containment therein of an accurately measured volume of a fluid specimen. An intermediate part of the tubular section 11 is passed through an opening through a mounting guide 25 and rigidly held therein via the mounting bolt $25_1$, and both the mounting guide 25 and the block 15 are mounted on the forward and rearward ends, respectively, of a slide or carriage 30. The carriage 30 is, in turn, mounted on a platform 40 raised on pillars $41_1$, $41_2$ ($41_3$, $41_4$ not shown) above the base 45. A portion of the tubular section 11 is also projected through an opening within the protective guide mount 26 which is carried on the forward end of the carriage 30, and movable therewith, and the terminal end of the tubular section 11 is affixed within the forward guide mount 27 which is rigidly secured upon the raised platform 40. The protective guide mount 26 carries a tubular seal $26_1$ through which the tubular member 11 is projected. A side opening $11_2$ (FIG. 4A) of tubular member 11 can be moved into and out of the seal $26_1$. The forward guide mount 27 carries a fluid specimen loading assembly 28 into which the capillary tube 14 can be contained, and then projected through to an inlet chamber 110 and beyond for subsequent injection of fluid specimen into inlet 120. The inlet chamber 110 is located in front of the raised platform 40, and in-line with the capillary fluid injector assembly 10 for receipt of a fluid specimen from the dispensing end of the tubular member 11 when the latter is physically thrust therein for aiding in the positive ejection and delivery of an accurately measured quantity of a fluid specimen into inlet 120.

The sample quantity adjustment mechanism 20 is constituted of a bolt or cylindrical member 21, provided with an externally threaded small diameter forward shank portion $21_1$ and large diameter rearward portion $21_2$ shaped to form a knurled knob, or handle. The axial opening therethrough includes a small diameter forward portion $18_1$, and an internally threaded large diameter portion $18_2$. The rearward face of the block 15, which is mounted upon the rearward end of carriage 30, is provided with an internally threaded enlarged opening $15_1$, coaxial with opening $18_1$ of tubular member 20 at the forward end of which is located a packing 19 containing a central opening through which the shaft 12 (FIG. 5B) is extended, and against which the forward end of the member 21 is pressed when threadably engaged within said opening $15_1$. Seal 19 is pushed against the inside face of block 15 and around the shaft 12 to form a seal. The rearward terminal end of shaft 12 is affixed to the forward end of the externally threaded forward end of bolt 21 threadably engaged within opening $18_2$, which on rotation in one direction retracts the shaft 12, and wire 13 from within the capillary tube 14, while rotation in the other direction advances the shaft 12, and wire 13 into the capillary tube 14 to increase or decrease, respectively, the volume of the capillary opening.

The capillary fluid injector assembly 10 is affixed via block 15 and mounting guide 25 upon the carriage 30 which is reciprocably movable upon a pair of parallelly disposed guide shafts $31_1$, $31_2$ (FIG. 1) which extend across an open rectangular shaped slot 32 within the horizontally disposed platform 40 mounted on pillars $41_1$, $41_2$ ($41_3$ and $41_4$ not shown), above the base 45 below which the motor driven carrousel feed tray 90 is rotatably mounted and supported upon a vertical spindle or shaft 92 located at the geometric center of the base 45. The guide shafts $31_1$, $31_2$ form rails upon which the capillary fluid injector assembly 10 is reciprocably movable via action of the cylinder-piston unit 46 mounted on the bottom side of the raised platform 40; at its forward end via its shaft or piston $46_1$ to the bottom of guide mount 25, and at its rearward and via a bolt connection $46_2$ to the bottom of platform 40. Thus, the carriage 30 and capillary fluid injector assembly 10 transported thereon via action of the cylinder piston unit 46 can be oscillated over the length of the guide shafts or rails 31 to project the capillary tube 14, after the tube 14 is loaded with a fluid specimen, into the inlet chamber 110, and then into inlet 120. The function of the carriage 30 is to transport the capillary feed injector assembly 10 between two positional extremities, a position or station wherein the capillary tube 14 is loaded with an accurately measured quantity of a fluid specimen, and a final position wherein the accurately measured quantity of the fluid specimen is injected into inlet 120 wherein the fluid specimen is transported into the analytical instrument. The carriage 30 is structured essentially as follows: the long outer edges of the flat rectangular plate constituting carriage 30 per se are provided with openings through which are fitted the guide shafts or rails $31_1$, $31hd 2$, the carriage 30 being movable thereon. The center of the flat rectangular plate constituting carriage 30 is also provided with an elongate opening, parallel and midway between said guide rail openings, within which is extended a shaft $26_2$ on which is provided an encircling helical spring (not shown). The forward end of the shaft $26_2$ is affixed to the forward intermediately positioned, guide mount 26 (FIG. 6A). The guide mount 26 is transported forwardly by the carriage 30 until it comes into contact with the fixed guide mount 27 at which time its forward movement ceases, the shaft $26_2$ then telescoping into the carriage 30 which said helical spring is contracted inside the opening within which it is housed to permit continued forward movement of the carriage 30 up to the point of contact between guide mounts 25, 26 as occurs during the moment of actual injection of the accurately measured amount of the fluid specimen into the septum inlet 120.

The movement of carriage 30 upon the horizontally disposed platform 40 is controlled via the double acting, pneumatic cylinder piston unit 46 mounted upon the lower side of the platform 40. The forward shaft end of the piston $46_1$ of said cylinder piston unit 46 is thus affixed to a lower edge of the guide member 25 of the carriage 30. The carriage 30 is thus moved forwardly by injection of air via line not shown into the rearward side of the cylinder piston unit 46 which causes extension of the shaft or piston $46_1$ from within the housing portion of the cylinder-piston unit 46. Initially, the protective guide mount 25 is carried forwardly, its first phase of forward movement continuing up to the time of contact between guide mount 26 and guide mount 27. The next phase of forward movement begins thereafter and continues up to the time of contact between guide mount 25 and guide mount 26. Thus, after contact between guide mounts 25, 26 and forward movement of the carriage 30 is discontinued, the shaft $26_2$ thereof is telescoped within the central opening of the plate constituting the carriage 30. The carriage 30 is retracted, or moved in the opposite direction upon the platform 40, by injection of air via a line not shown into the forward end of the cylinder piston unit 46, the shaft or piston $46_1$ being withdrawn into the housing of the cylinder-piston unit 46. The guide mount 26 initially remains in contact with the guide mount 27, and it is then separated and retracted rearwardly away from guide mount 27 after the full reextension of shaft $26_2$ from within its elongate opening via action of said coiled helical spring (not shown).

In the extreme rearward position of carriage 30, as best shown by reference to FIGS. 4 and 4A, the capillary tube 14 of the capillary fluid injector assembly 10 lies within the fluid diversion and specimen loading assembly 28 of the guide mount 27, affixed at the forward end of raised platform 40. This is the position of the capillary tube 14 when it is loaded with a fluid specimen received via line $61_5$ from probe $61_1$ of the injector feed assembly 50. The capillary tube 14, the wire 13 which is directly connected to the capillary tube 14, and shaft 12 (FIG. 5B) which is connected to the wire 13 lie within the bore of the tube 11; the capillary tube 14 lying at the end of the tube 11 while the rearward end of the shaft 12 is extended from within and connected to the externally threaded end of the bolt or cylindrical member 21. Rotation of the bolt or externally threaded member 21, of the sample adjustment quantity mechanism 20, via the manual (or mechanical) manipulation of the knurled end knob $21_2$ thereof actuates rod 12 and positions the wire 13 within the capillary tube 14 to the extent desired, the greater the extent of the wire 13 into the capillary opening the lesser the volume of fluid specimen which can be loaded therein; and conversely, the lesser the extent of the wire 13 into the capillary opening the greater the amount of fluid specimen which can be loaded therein. The fluid specimen loading assembly unit 28 forms a loading chamber. The chamber within which the capillary tube 14 is contained is constituted of a cup-like container $28_1$ the closed forward end of which is provided with a central opening $28_{1A}$, a gas impervious diaphragm or seal $28_2$ located at the front closed-end of the container $28_1$, a tubular resilient plastic member $28_3$ the central tubular opening $28_{3A}$ of which is communicated with a lateral opening $28_{3B}$ extending therethrough, and an open centered end cover or plug $28_4$ threadably engaged with the rearward internally threaded end of the cup-like container $28_1$ to retain the diaphragm $28_2$ and tubular plastic member $28_3$ in place within said cup-like container $28_1$. Tubular connections extending from the two sides of the lateral opening $28_{3B}$ provide means for the attachment thereto of line $61_5$ for passage of a pressurized fluid specimen from the probe portion of the injector feed assembly 50 to the fluid specimen loading assembly 28, and line $61_6$ for the removal of fluid specimen, or waste fluid therefrom. In loading position, the forward open end of the capillary tube 14 lies within the tubular opening $28_{3A}$ at a point where fluid from the injector feed assempy 50 flowing through lateral opening $28_{3B}$ will contact the open end of the capillary tube 14. Consequently, a fluid specimen passed via line $61_5$ through lateral opening $28_{3B}$ flows across and a portion thereof flows into and fills the capillary bore of capillary tube 14 via capillary action. Excess of the fluid specimen, or solvent and gas as used in cleaning, purging and drying the device exits from the loading assembly 28 via line $61_6$.

The inlet chamber 110 is located behind and in line with the septum inlet 120 with which it forms an integral unit. It is constituted of a tubular segment 111, the axial opening $111_1$ of which is coaxial with a forward internally threaded enlarged opening $111_2$ to which it is threadably engaged to septum inlet 120, also constituted of a tubular body 121 provided with an axial opening $121_1$. A diaphragm or seal $111_3$ is located at the rear of the opening $111_1$ of tubular body 111, and another seal $111_4$ is located at the forward end of the tubular body 111 and held in place by the physical presence of the relatively large diameter externally threaded rearward end of tubular member 121 threadably engaged upon the tubular body 111. The axial opening $121_1$ of septum inlet 120 and axial opening $111_1$ of inlet chamber 110, both of which are also coaxial with opening $11_1$ of the tubular member 11, are each provided with communicating lateral openings $121_2$ and $111_5$, respectively, the latter opening $111_5$ extending through the diameter of the tubular body 111. The septum inlet 120 is provided with a second lateral opening $121_3$ through which a fluid specimen, on injection, is carried by carrier gas to the analytical instrument. The lateral openings $121_2$ and $111_5$ of the septum inlet 120 and inlet chamber 110, respectively, are connected via a valved line 112, and a valved line 113 provides further communication with the axial opening $111_1$ of inlet chamber 110. Lines 112 and 113, respectively, can be opened or closed via valves $112_1$ and $113_1$, respectively. Pressure between the chambers formed by axial opening $111_1$ (which lies between seals $111_3$ and $111_4$) and axial opening $121_1$ (located forward of seal $111_4$) can be equalized by opening line 112 via use of valve $112_1$; or maintained at different pressures by closure of this line. The wall of tubular member 11, as best shown by specific reference to FIG. 4A, is provided with an opening $11_2$ which, when contained within the tubular opening through seal $26_1$, is closed. When the capillary tube 14 at the dispensing end of tubular member 11 is loaded and projected through the seal or diaphragm $111_4$ into the septum inlet 120, and the side opening $11_2$ of tubular member 11 is contained within inlet chamber 110 a positive pressure can be applied to positively expel the fluid specimen from the tube 14 into the inlet 120.

(B) The purpose of the injector feed assembly 50 is to pick up a fluid specimen from a septum covered vial 91 carried and positioned by the carrousel feed tray 90 beneath the probe assembly 60. Fluid specimen is withdrawn from a vial and conveyed to the capillary fluid injector assembly 10. The injection feed assembly 50 includes means, suitably a double acting cylinder piston unit 51, for vertical reciprocation of the probe assembly 60 with which it is an integral part. The piston 52 of the cylinder piston unit 51 thus carries a reciprocable hollow probe assembly 60 the lower terminal end of which can be projected through the septum of a septum covered vial 91 to pick up or withdraw a fluid specimen therefrom for transfer to the capillary fluid injector assembly 10.

The details of the injector feed assembly 50 is best described by reference to FIGS. 1–4. In these figures the probe assembly 60 is in lowered position, the piston 52 being nearly bottomed out within the housing or barrel of the cyclinder piston unit 51. Referring to FIGS. 3 and 4 the probe assembly 60 is shown after having been lowered for the terminal end thereof to pierce the septum of a vial 91 for withdrawal of a fluid specimen therefrom for conveyance to the capillary fluid injector assembly 10. The cylinder piston unit 51 is entirely conventional. The principle components of the injector feed assembly 50 includes the piston 52 of the cylinder piston unit 51, which carries a probe assembly 60 which can be vertically reciprocated by alternate injection of air, or other pressurized fluid, against the head of the piston contained within the housing or barrel portion of the cylinder piston unit 51. The piston 52, and consesequently the probe assembly 60, is reciprocated by injection of air via a line not shown into the top end of the housing of the cylinder piston unit 51 to move the piston 52 downwardly, and alternatively into the lower end of the housing via a line not shown to move the piston 52 upwardly. Thus, the septum of a vial 91 transported into position beneath the probe assembly 60 is penetrated by downward projection of the probe assembly 60 carried by piston 52 when air is injected into the upper end of the housing of the cylinder piston unit 51. It is withdrawn from a vial 91 via injection of air into the lower end of the housing of the cylinder piston unit 51.

The details of the probe assembly 60, and its function, are best shown, described and illustrated by direct reference to FIG. 4. The lower end of probe assembly 60, as shown in this figure, is projected into a vial 91 which contains a fluid specimen which is to be delivered to the capillary fluid injector assembly 10. The probe assembly 60 per se is constituted of a pair of concentrically mounted hollow needles; an inner needle $61_1$ of relatively small diameter contained within a larger diameter needle $61_2$. An annulus between the inner needle $61_1$ and outer needle $61_2$ provides an internal conduit within which a pressurized gas, suitably air, can be transmitted through an inlet as via a connecting tube 62, the gas entering vial 91 via the opening or exit port $61_3$. Since the gas cannot escape through the septum $91_1$, which is held tightly atop the via 91 by a cover $91_2$, the fluid contents of the vial are pressurized by the entering gas, and fluid specimen is forced into the entry port $61_4$, the fluid specimen ascending through the axial opening or bore of needle $61_1$ and exiting the connecting tubing $61_5$ whereupon it flows past the tip or terminal end of the capillary opening with the capillary fluid injector assembly 10 to exit therefrom via line $61_6$.

(C) The function of the carrousel feed tray 90 is to transport fluid specimen filled vials 91 in seriatim one behind the other to a location for pick up and transport of the fluid contents by the injector feed assembly 50 to the capillary fluid injector assembly 10. The carrousel feed tray 90 is constituted of a rotary table which can contain a plurality of fluid specimen-containing vials 91, and it is rotated about a spindle or shaft 92 at the geometric center of the table. Suitably, the upper ends of the vials 91 are sealed with an elastometer septum 911 to prevent leakage and contamination, and permit pressurization. As the vials 91 are moved into position beneath the probe assembly 60 of the injector feed assembly 50, the probe 60 is thrust downwardly so that the lower terminal pointed or tapered end of the outer hollow needle $61_2$ penetrates the septum $91_1$ of a vial 91 in an initial step in preparation for pick up and transport of a fluid specimen to the capillary fluid injector assembly 10.

An operating cycle is conveniently described, principally by reference to FIGS. 4 through 6B, these figures depicting the pick up of a fluid specimen from a septum covered vial and delivery thereof to the capillary fluid injector assembly 10, injection of a preselected accurately measured quantity of a fluid specimen into the inlet of an analytical instrument as follows:

(a) Referring first to FIGS. 1–3, and 4, the probe assembly 60 of the injector feed assembly 50 is shown in lowered position; having been lowered from an elevated, or raised position, the piston 52 being extended from the housing or barrel of the cylinder piston unit 51. The capillary fluid injector assembly 10 is positioned for loading the capillary tube 14 with a fluid specimen from a vial.

The carriage 30, as shown by reference to FIGS. 1–3, and 4 is in its extreme rearward position upon the raised horizontal platform 40, the piston $46_1$ of the cylinder piston 46 being withdrawn within its housing, or barrel. The terminal end of the probe assembly 60 near the bottom of its stroke has penetrated the septum of a vial 91, and a pressurized gas is injected via line 62 into the annulus between the pair of probe needles $61_1$, $61_2$, the gas exiting via the opening $61_3$ to pressurize the inside of a vial 91 (FIG. 4). The fluid specimen of the vial 91, under pressure is forced via opening $61_4$ into the inner probe needle $61_1$ whereupon it is conveyed via line $61_5$ to the fluid specimen loading assembly unit 28, the fluid specimen entering into the channel or opening $28_{3B}$ whereupon, on passing axial opening $28_{3A}$, a portion of the fluid specimen is picked up by capillary tube 14 via capillary action. Excess of the fluid specimen is passed via line $61_6$ to waste.

(b) The fluid specimen, measured in accurately measured quantity within the capillary tube 14 must now be injected into septum inlet 120. Reference is now made to FIGS. 5, 5A and 5B. The carriage 30 is now moved forwardly to its next position via injection of gas into the rearward end of the cylinder piston unit 46, the piston $46_1$ being projected outwardly from its housing. The tubular member 11 is guided along its path, and protected from bending by the protective guide mount 25 which moves forward with the carriage 30, upon which it is mounted, until the forward protective guide mount 26 comes into contact with guide mount 27.

During this movement of the carriage 30, the diaphragms, or seals $28_2$, $111_3$ are penetrated by the dispensing end of the capillary fluid injector 10 and the capillary tube 14, loaded with a fluid specimen, is thrust into the axial opening $111_1$ of inlet chamber 110. The capillary tube 14 comes to rest within inlet chamber 110 between the diaphragms, or seals $111_3$, $111_4$ (FIG. 5B). As the capillary tube 14 is about to enter into the inlet chamber 110, solenoid valve $112_1$ is opened to equalize the pressure between the inlet chamber 110 and septum inlet 120. Solenoid valve $113_1$ is closed.

Figure 6:
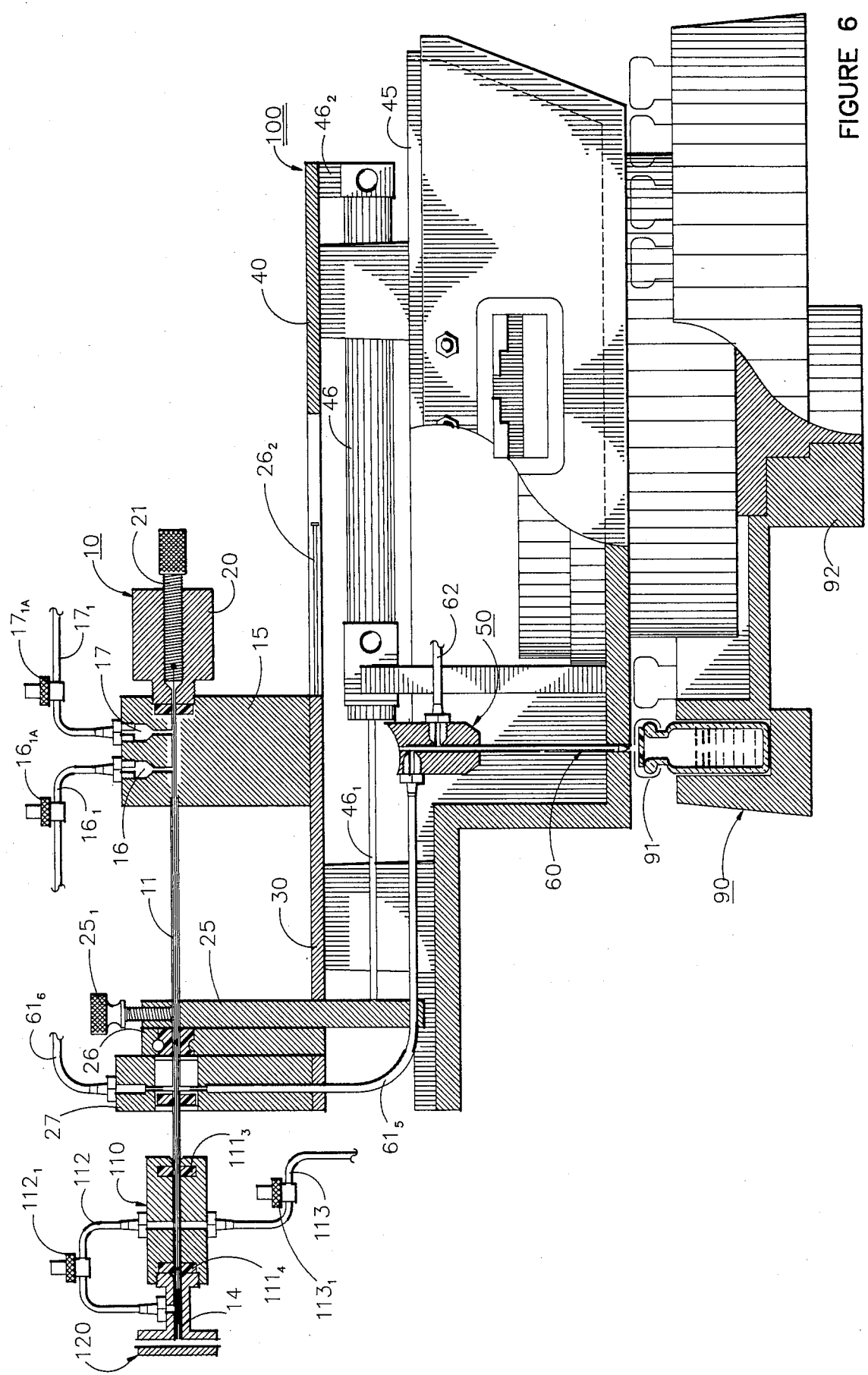

(c) Forward movement of the carriage 30 is continued. Reference is now made to FIGS. 6, 6A and 6B. As forward movement of the carriage 30 is continued, the shaft portion $26_2$ of the guide mount 26 telescopes within the plate constituting the body of the carriage 30, further continuously protecting and guiding the tubular element 11 as it does so. The movement of the carriage 30 stops when the fixed guide mount 25, in effect the Vertical front wall of the carriage 30, contacts the rearward face of guide mount 26 which comes to rest after contact with the forward fixed guide mount 27. The continued forward movement of the carriage 30 thrusts the capillary tube 14 of elongate tubular body 11 through the diaphragm or seal $111_4$, and the capillary tube 14 now lies entirely within the septum inlet 120. As the capillary tube 14 moves into the septum inlet 120 solenoid valve $112_1$ is closed, solenoid valve $113_1$ is activated and opened, and gas (e.g., air) at pressure higher than in septum inlet 120 enters via valved line 113 into opening $11_2$ of the tubular member 11 to positively expel, or force injection of the fluid specimen into the analytical instrument. Thus, the fluid specimen is ejected from the capillary tube 14 to enter into lateral opening $121_3$ where it is swept by carrier gas into the instrument.

(d) The cylinder piston unit 51 of the injector fluid assembly 50 can now be reactuated and the piston 52 moved upwardly to withdraw the probe assembly 60 from the vial 91.

(e) The feed tray 90 can now be rotated to move the next loaded vial into position for pick up by the probe assembly 60, after cleaning, purging and drying.

(f) The carriage 30 can now be retracted to its initial load position, as shown e.g., by reference to FIGS. 4 and 4A. With the capillary fluid injector assembly 10 so positioned a cleaning solvent and air, respectively, can be passed through the axial opening $11_1$ to clean and then dry the passageway and thus avoid any possibility of contamination from a previously injected fluid specimen. The cleaning fluid can, e.g., be introduced via line $16_1$ by the actuation and opening of solenoid valve $16_{1A}$, the cleaning fluid passing through the axial passageway $11_1$ to clean shaft 12, wire 13 and capillary tube 14, the purging fluid then passing into the opening 28$_{3B}$ wherefrom the stream is removed as waste via line 61$_6$. In generally similar fashion the shaft 12, wire 13, and capillary tube 14 are dried by cutting off the flow of cleaning fluid via actuation and closure of solenoid valve 16$_{1A}$, and thereafter actuating and opening solenoid valve 17$_{1A}$ to inject a stream of dry air into the axial passageway 11$_1$. After the drying step is completed solenoid valve 17$_{14}$ is again closed.

The capillary fluid injector 10, in its initial load position, cleaned and dried, is now ready for beginning a new cycle of operation. The new cycle beginning with the introduction of the probe assembly 60 into the next vial 91 delivered in position by rotation of carrousel feed tray 90.

It is apparent that various modifications and changes can be made without departing the spirit and scope of the present invention. The apparatus is constructed of materials substantially inert or nonreactive to the chemical or corrosive action of the fluid specimens to be measured and dispensed. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The poly-fluorinated ethylene polymers, notable among which is polytetrafluoroethylene (Teflon), are particularly outstanding. Conventional resilient or plastic-like materials, such as natural or synthetic rubbers can also be employed.

The capillary fluid injector assembly, the injector feed assembly, particularly the needle and probes, the piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like as well as the suggested mode or particular sequence of withdrawing or delivering fluids, can be made without departing the spirit and scope of the invention, as will be apparent to those skilled in this art.

Having described the invention, what is claimed is:

1. In capillary fluid injection apparatus for the measurement and injection of a preselected quantity of a fluid specimen into the inlet of an analytical instrument wherein is included
    an elongate tubular body formed by an enclosing wall, and
    a capillary opening located at the dspensing end of said elongate tubular body into which a fluid specimen can be loaded,
    the improvement comprising
    a small diameter wire which can be extended into and retracted from within the capillary opening of said elongate tubular body to provide an annulus of capillary dimension, and
    a sample quantity adjustment means operatively associated with said small diameter wire to move the small diameter wire and vary the volume of said capillary opening to accommodate the quantity of a fluid specimen preselected for injection into the inlet of said analytical instrument.

2. The apparatus of claim 1 wherein the wall of the elongate tubular body of said capillary fluid injection apparatus rearwardly of the capillary opening contains a side opening, and the combination further includes a tubular inlet chamber adjoined with the inlet to the analytical instrument, the capillary opening of the elongate tubular body of said capillary fluid injector on forward movement being extensible first into the tubular inlet chamber and then into the inlet of said analytical instrument adjoined thereupon, the tubular openings through said tubular inlet chamber and inlet of said analytical instrument being coaxial, a first gas impervious seal separating the tubular openings of the tubular inlet chamber and inlet to the analytical instrument, a second gas impervious seal being located in said tubular inlet chamber rearwardly of and separated from said first gas impervious seal, the elongate tubular body of said capillary fluid injector being projectable through both of said gas impervious seals while the wall opening therein is contained within said inlet chamber, the inlet chamber and inlet to said analytical instrument being connected via a first valved line which can be opened to equalize the pressure between the inlet chamber and inlet to said analytical instrument, and a second valved line connected to said inlet chamber which can be opened to pressurize the inlet chamber, and closed off from communication with the inlet chamber, whereby the capillary opening at the dispensing end of the elongate tubular body when loaded with an accurately measured preselected quantity of a fluid specimen, with the pressure equalized between said tubular inlet chamber and said inlet to the analytical instrument, can be physically projected through said second gas seal into said tubular inlet chamber, then through the first gas impervious seal into said inlet to the analytical instrument, such that gas can be injected via said second valved line into the wall opening of said elongate tubular body to positively expel the fluid specimen from the capillary opening into the inlet to the analytical instrument.

3. The apparatus of claim 2 wherein the combination further includes a fluid specimen loading chamber rearwardly of said tubular inlet chamber within which said fluid specimen can be loaded into the capillary opening at the dispensing end of the elongate tubular body.

4. The apparatus of claim 3 wherein the fluid specimen loading chamber is comprised of an assembly which includes
    a cup-like container, the closed forward end of which is provided with a central opening,
    a gas impervious seal located at the front closed end of the cup-like container,
    a tubular resilient member located rearwardly of said gas impervious seal, the axial opening of which is communicated with a lateral opening extending therethrough, the lateral opening on one side of the axial opening in communication therewith providing an inlet for the introduction of a fluid specimen while the other side of the lateral opening provides an outlet for the exit of excess of the fluid specimen, whereby, when the capillary opening at the dispensing end of the elongate tubular body of the capillary fluid injection device is thrust into the axial opening through said tubular resilient member to lie therein and fluid specimen is passed through said lateral opening the fluid specimen will fill said capillary opening via capillary action.

5. The apparatus of claim 4 wherein the gas impervious seal and tubular resilient member are retained within the cup-like member by an open centered cap affixed to the rearward end of said cup-like container.

6. The apparatus of claim 5 wherein the rearward end of the cup-like member is internally threaded, the open centered cap is externally threaded and the cap is threadably engaged to the rearward end of the cup-like member.

7. The apparatus of claim 5 wherein the tubular resilient member is constituted of plastic.

8. The apparatus of claim 1 wherein the sample quantity adjustment means is comprised of a tubular block within the tubular opening of which the terminal end opposite the dispensing end of the elongate tubular body is fitted, the tubular openings of the tubular block and elongate tubular body are coaxial, a rod extends through said coaxial tubular openings, the forward end of which is affixed to the small diameter wire contained with the capillary opening at the dispensing end of said elongate tubular body, and the rearward end of said rod is affixed to member which is mounted and reciprocably movable within the tubular opening of said tubular block such that the small diameter wire can be advanced and retracted within the capillary opening of the elongate tubular body to vary its volume.

9. The apparatus of claim 8 wherein the reciprocably movable member to which the rearward end of said rod is affixed is an externally threaded bolt, the tubular opening of the tubular block at its rearward face is internally threaded, and the bolt is threadably engaged therewith so that rotation of the bolt in one direction will advance the rod and small diameter wire affixed thereto, and rotation of the bolt in the opposite direction will retract the rod and small diameter wire affixed thereto.

10. In combination, fluid capillary injection apparatus for the measurement and injection of a preselected quantity of a fluid specimen into the inlet of an analytical instrument which comprises an elongate tubular body formed by an enclosing wall, the wall containing a side opening, a capillary opening located at the dispensing end of said elongate tubular body, forward of said side opening, into which a fluid specimen can be loaded, a small diameter wire which can be extended into and retracted from within the capillary opening of said elongate tubular body to provide an annulus of capillary dimension, and a sample adjustment means characterized as a tubular block within the tubular opening of which the terminal end opposite the dispensing end of the elongate tubular body is fitted, the tubular openings of the tubular block and elongate tubular body are coaxial, a rod extends through said coaxial tubular openings, the forward end of which is affixed to the small diameter wire contained with the capillary opening at the dispensing end of said elongate tubular body, and the rearward end of said rod is affixed to a member which is mounted and reciprocably movable within the tubular opening of said tubular block such that the small diameter wire can be advanced and retracted with the capillary opening of the elongate tubular body to vary its volume.

11. The apparatus of claim 10 wherein the reciprocably movable member to which the rearward end of said rod is affixed is an externally threaded bolt, the tubular opening of the tubular block at its rearward face is internally threaded, and the bolt is threadably engaged therewith so that rotation of the bolt in one direction will advance the rod and small diameter wire affixed thereto, and rotation of the bolt in the opposite direction will retract the rod and small diameter wire affixed thereto.

12. The apparatus of claim 10 wherein the combination further includes a tubular inlet chamber adjoined with and rearward of the inlet to the analytical instrument, the tubular openings of the tubular inlet chamber and inlet to the analytical instrument are coaxial and separated by a first gas impervious seal, a second gas impervious seal being located in said tubular inlet chamber rearwardly of and separated from said first gas impervious seal, the elongate tubular body of said capillary fluid injector being projectable through both of said gas impervious seals while the side wall opening thereof is contained within said tubular inlet chamber the inlet chamber and inlet to said analytical instrument being connected via a first valved line which can be opened to equalize the pressure between the inlet chamber and inlet to said analytical instrument, and a second valved line connected to said inlet chamber which can be opened to pressurize the inlet chamber, and closed off from communication with the inlet chamber, whereby the capillary opening at the dispensing end of elongate tubular body when loaded with an accurately measured preselected quantity of a fluid specimen, with the pressure equalized between said tubular inlet chamber and said inlet to the analytical instrument, can be physically projected through said second gas seal into said tubular inlet chamber, then through the first gas impervious seal into said inlet to the analytical instrument, such that gas can be injected via said second valved line into the wall opening of said elongate tubular body to positively expel the fluid specimen from the capillary opening into the inlet to the analytical instrument.

13. The apparatus of claim 12 wherein the combination further includes a fluid specimen loading chamber rearwardly of said tubular inlet chamber within which said fluid specimen can be loaded into the capillary opening at the dispensing end of the elongate tubular body.

14. The apparatus of claim 13 wherein the fluid specimen loading chamber is comprised of an assembly which includes a cup-like container, the closed forward end of which is provided with a central opening, a gas impervious seal located at the front closed end of the cup-like container, a tubular resilient member located rearwardly of said gas impervious seal, the axial opening of which is communicated with a lateral opening extending therethrough, the lateral opening on one side of the axial opening in communication therewith providing an inlet for the introduction of a fluid specimen while the other side of the lateral opening provides an outlet for the exit of excess of the fluid specimen, whereby, when the capillary opening at the dispensing end of the elongate tubular body of the capillary fluid injection device is thrust into the axial opening through said tubular resilient member to lie therein and fluid specimen is passed through said lateral opening the fluid specimen will fill said capillary opening via capillary action.

15. In fluid injection apparatus useful for the measurement and injection of preselected quantities of a fluid specimen into an inlet to an analytical instrument which includes the combination of (A) a fluid injection assembly inclusive of a fluid injector into which a fluid specimen can be loaded, and means for injection of the fluid specimen from said fluid injector into said inlet, (B) an injector feed assembly comprised of a probe sub-assembly inclusive of a pair of hollow needles which provide conduit means for the pick up of said fluid specimen from a vial and transport of said fluid specimen to said fluid injector, and (C) a magazine for transporting one or more fluid specimen-containing septum sealed vials for pick up by said pair of hollow needles of said probe subassembly for delivery to said fluid injector via thrust of the probe through the septum of a vial, pressurizing the contents of the vial by delivery of gas from a source through a first of said hollow needles of said probe sub-assembly to produce flow of fluid specimen from the vial into the second of the set of hollow needles for transport through the probe sub-assembly to said fluid injector, a platform located adjacent the magazine (C) and carriage reciprocably mounted on said platform atop which the fluid injector assembly (A) is mounted, the improvement wherein the fluid injector assembly (A) comprises the combination of an elongate tubular body formed by an enclosing wall, the wall containing a side opening, a capillary opening located at the dispensing end of said elongate tubular body, forward of said side opening, into which a fluid specimen can be loaded, a small diameter wire which can be extended into and retracted from within the capillary opening of said elongate tubular body to provide an annulus of capillary dimension, and a sample adjustment means characterized as a tubular block within the tubular opening of which the terminal end opposite the dispensing end of the elongate tubular body is fitted, the tubular openings of the tubular block and elongate tubular body are coaxial, a rod extends through said coaxial tubular openings the forward end of which is affixed to the small diameter wire contained with the capillary opening at the dispensing end of said elongate tubular body, and the rearward end of said rod is affixed to a member which is mounted and reciprocably movable within the tubular opening of said tubular block such that the small diameter wire can be advanced and retracted with the capillary opening of the elongate tubular body to vary its volume, a fluid specimen loading chamber mounted on the platform forward of the carriage into which the capillary opening at the dispensing end of said elongate tubular body can be extended and into which a fluid specimen picked up from a vial by the probe sub-assembly of the injector feed assembly (B) can be introduced for loading into said capillary opening, and a tubular inlet chamber adjoined with and rearward of the inlet to the analytical instrument, the tubular openings of the tubular inlet chamber and inlet to the analytical instrument are coaxial and separated by a first gas impervious seal, a second gas impervious seal being located in said tubular inlet chamber rearwardly of and separated from said first gas impervious seal, the elongate tubular body of said capillary fluid injector being projectable through both of said of said gas impervious seals while the side wall opening thereof is contained within said tubular inlet chamber, the inlet chamber and inlet to said analytical instrument being connected via a first valved line which can be opened to equalize the pressure between the inlet chamber and inlet to said analytical instrument, and a second valved line connected to said inlet chamber which can be opened to pressurize the inlet chamber, and closed off from communication with the inlet chamber, whereby the capillary opening at the dispensing end of elongate tubular body when loaded with an accurately measured preselected quantity of a fluid specimen, with the pressure equalized between said tubular inlet chamber and said inlet to the analytical instrument, can be physically projected through said second gas seal into said tubular inlet chamber, then through the first gas impervious seal into said inlet to the analytical instrument, such that gas can be injected via said second valved line into the wall opening of said elongate tubular body to positively expel the fluid specimen from the capillary opening into the inlet to the analytical instrument.

16. The apparatus of claim 15 wherein the fluid specimen loading chamber is comprised of an assembly which includes a cup-like container the closed forward end of which is provided with a central opening, a gas impervious seal located at the front closed end of the cup-like container, a tubular resilient member located rearwardly of said gas impervious seal the axial opening of which is communicated with a lateral opening extending therethrough, the lateral opening on one side of the axial opening in communication therewith providing an inlet for the introduction of a fluid specimen while the other side of the lateral opening provides an outlet for the exit of excess of the fluid specimen whereby, when the capillary opening at the dispensing end of the elongate tubular body of the capillary fluid injection device is thrust into the axial opening through said tubular resilient member to lie therein and fluid specimen is passed through said lateral opening the fluid specimen will fill said capillary opening via capillary action.

* * * * *